United States Patent [19]

Valle et al.

[11] Patent Number: 4,704,469

[45] Date of Patent: Nov. 3, 1987

[54] PREPARATION OF HALOGENATED PHENOLS

[75] Inventors: Francesco D. Valle, Padova; Aurelio Romeo, Rome, both of Italy

[73] Assignee: Fidia S.p.A., Abano Terme, Italy

[21] Appl. No.: 684,733

[22] Filed: Dec. 21, 1984

[30] Foreign Application Priority Data

Dec. 21, 1983 [IT] Italy ................. 49556 A/83

[51] Int. Cl.$^4$ ............................. C07C 69/76
[52] U.S. Cl. ................... 560/065; 562/476; 564/412; 564/440; 564/442; 568/765; 260/512 R
[58] Field of Search ......... 560/065; 562/476; 564/412, 440, 442; 568/765; 260/512

[56] References Cited

FOREIGN PATENT DOCUMENTS

| | | |
|---|---|---|
| BE871315 | 2/1979 | Belgium . |
| 141751 | 6/1897 | Fed. Rep. of Germany ...... 384/239 |
| 1268389 | 5/1968 | Fed. Rep. of Germany . |
| 2422772 | 1/1975 | Fed. Rep. of Germany . |
| 2616479 | 11/1977 | Fed. Rep. of Germany . |
| 3044128 | 7/1982 | Fed. Rep. of Germany . |
| 147424 | 4/1981 | German Democratic Rep. . |
| 52094 | 5/1973 | Japan . |
| 111849 | 9/1981 | Japan . |
| 34530 | 2/1984 | Japan . |
| 663552 | 12/1951 | United Kingdom ............... 84/14 |
| 1136525 | 12/1968 | United Kingdom ............... 172/576 |

OTHER PUBLICATIONS

Ausl. J. Chem. 25(7) 1537–1542 1972.
Weitl F. J. Org. Chem. 41(11) 2044–2045, 1976.
Komavek Joseph, Collect Czech Chem. Commun 46(3) 708–716, 1981.
Vaselinovic Draz. Glas Hem Drus. Beograd 48(9) 619–625, 1983.

EPO Search Report, EPO Application No. 84115842.1.
Chemical Abstracts, vol. 63, Dec. 20, 1985, No. 13, pp. 17102 and 17949–17950.

Primary Examiner—Paul J. Killos
Attorney, Agent, or Firm—Birch, Stewart, Kolasch & Birch

[57] ABSTRACT

A method for the preparation of 2-halogenoresorcinols having the following formula I

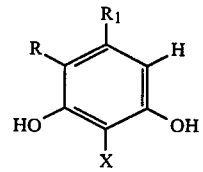

where X represents a halogen atom and R and $R_1$ may be the same or different and represent a hydrogen atom or a free organic functional or functionally modified group or a hydrocarbon group, which may be substituted by one or more free organic functional or functionally modified groups and R and $R_1$ jointly may also represent a free organic functional or functionally modified group or a hydrocarbon group which may be substituted by one or more free organic functional or functionally modified groups, and esters, ethers, or salts thereof.

The method comprises sulfonating the corresponding resorcinols which do not contain a halogen in the 2-position and then halogenating the sulfonic acids thus obtained. The halogenated sulfonic acids thereby obtained are subsequently protodesulfonated by acid hydrolysis and, if desired, any functional groups which may be present can be modified.

33 Claims, No Drawings

PREPARATION OF HALOGENATED PHENOLS

BACKGROUND AND FIELD OF THE INVENTION

The present invention relates to a method for the preparation of 2-halogenoresorcinols having the following formula I

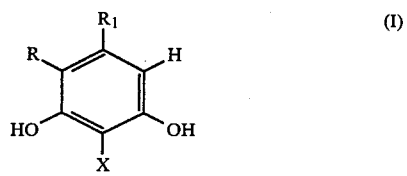

where X represents a halogen atom and R and $R_1$ may be the same or different and represent a hydrogen atom or a free organic functional or functionally modified group or a hydrocarbon group, which may be substituted by one or more free organic functional or functionally modified groups and R and $R_1$ jointly may also represent a free organic functional or functionally modified group or a hydrocarbon group which may be substituted by one or more free organic functional or functionally modified groups, and esters, ethers, or salts thereof.

The method of the invention comprises sulfonating the corresponding resorcinols which do not contain a halogen in the 2-position and then halogenating the sulfonic acids thus obtained. The halogenated sulfonic acids thereby obtained are subsequently protodesulfonated by acid hydrolysis and, if desired, any functional groups which may be present can be modified.

The halogenoresorcinols of formula (I) are compounds which in recent years have become industrially important. For example, in U.S. Pat. No. 4,296,039 it is disclosed that 2-chlororesorcinol and 2-bromoresorcinol can be used to prepare coumarins which are halogenated in the 8-position and which may be used for medicinal purposes. The known methods for preparing 2-halogenoresorcinols do not give satisfactory results. In particular, direct halogenation of the resorcinols produces halogen-derivative mixtures which are difficult to separate; and the transformation of the resorcinols in dihydroresorcinol, followed by halogenation and the elimination of hydrohalogenacids with the formation of halogenoresorcinols, has proved to be difficult to perform on an industrial scale.

OBJECTS AND SUMMARY OF THE INVENTION

It is therefore one object of the present invention to provide a process for the preparation of halogenoresorcinols which is efficient for industrial scale production.

It is another object of the invention to provide a process for the preparation of halogenoresorcinols in a high yield and without the need for difficult separation procedures.

These and other objects of the present invention are accomplished by providing a method comprising sulfonating resorcinols which do not contain a halogen in the 2-position and then halogenating the resulting sulfonic acids. The halogenated sulfonic acids are subsequently protodesulfonated by acid hydrolysis and, if desired, any functional groups which may be present can be modified.

DETAILED DESCRIPTION OF THE INVENTION

The present invention concerns the preparation of halogenated phenols. Specifically, the method of the invention provides a new procedure for the preparation of 2-halogenoresorcinols of formula (I)

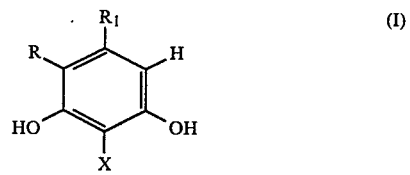

where X represents a halogen atom and R and $R_1$ may be the same or different and represent a hydrogen atom or a free organic functional or functionally modified group or a hydrocarbon group, which may be substituted by one or more free organic functional or functionally modified groups, and R and $R_1$ jointly may also represent a free organic functional or functionally modified group or a hydrocarbon group, which may be substituted by one or more free organic functional or functionally modified groups. The invention also relates to the preparation of esters, ethers and salts of the 2-halogenoresorcinols of formula (I).

In formula (I), the halogen atom X may be chlorine, bromine, iodine or fluorine, but is preferably chlorine, bromine or iodine.

The above-mentioned functional organic groups are, for example, hydroxyl, carboxylic and amine groups, free or functionally modified, and halogens. Of the functionally modified hydroxyl groups, particularly important are etherified groups, especially with lower aliphatic alcohols, for instance those with from 1–7 carbon atoms, such as methyl, ethyl, normal propyl and isopropy alcohols, the butyl and amyl alcohols, or aromatic alcohols such as benzy or phenethyl alcohol. Other functionally modified hydroxyl groups are esterified hydroxyl groups, particularly with an organic acid having between 1 and 15 carbon atoms, such as lower aliphatic acids with a maximum of 7 carbon atoms, such as formic, acetic and propionic acids, the butyric acids; or the dibasic acids, such as succinic and malonic acid; or the aromatic acids, such as benzoic acid and its derivatives; or sulfonic acids, such as the alkylsulfonic acids with between 1 and 4 carbon atoms; or the arylsulfonic monocyclic acids, such as p-toluenesulfonic acid.

Functionally modified carboxylic groups are for example esterified carboxylic groups, preferably with lower aliphatic alcohols with between 1 and 7 carbon atoms or with araliphatic alcohols, such as benzyl and phenethyl alcohol. Of the functionally modified carboxylic groups, the nitrile group —CN and the amide groups are important, such as the amide group —$CONH_2$ or amide groups derived from secondary amines.

The amine groups can be the primary amine group —$NH_2$ or a secondary amine group —NH—$R_2$ or a tertiary group

where $R_2$, $R_3$ and $R_4$ are nonsubstituted hydrocarbon groups, such as one of those discussed below as possibilities for R and $R_1$. The primary or secondary amine group may also be functionally modified, in particular it may be acylated, for example with one of the acyl groups mentioned above in relation to the functionally modified hydroxyl groups.

The hydrocarbon groups for R and/or $R_1$ of formula (I), and $R_2$, $R_3$ and $R_4$ discussed above, may be aliphatic, aromatic or alicyclic and each of these groups may be substituted by hydrocarbon residues of the other series. These groups may be $C_{1-12}$ alkyls, preferably $C_{1-7}$ alkyls, or cycloalkyls, particularly $C_{3-7}$ cycloalkyls and may be substituted by one or more groups, for example by 1 to 3 alkyl groups, preferably with a maximum number of 4 carbon atoms, and especially by methyl groups.

In the case of R and $R_1$ jointly representing a hydrocarbon group, it is preferably an alkylene group with, for example, between 1 and 7 carbon atoms. Each of the above-mentioned hydrocarbon groups may be substituted by one or more, preferably by between one and three, organic functional groups, for example by one of the functional groups mentioned above. It is especially preferred that the aromatic hydrocarbon groups, such as phenyl groups, may be substituted with one or more halogen atoms, particularly between 1 and 3 halogens.

preferably those derived from the hydrocarbon groups or from the above-mentioned organic acids.

The procedure perfected by the inventors of the present invention comprises, in the first stage, the sulfonation of a resorcinol of formula (II), where R and $R_1$ have the same significance as in formula (I). This sulfonation leads to the resorcinolsulfonic acids (IV) when R is different from hydrogen and to the resorcinolsulfonic acids of formula (III) when R is hydrogen. In both cases, R and/or $R_1$ may be modified whenever they represent, in the original compounds, groups which are hydrolyzable in the process of sulfonation, such as acyloxy or acylamine groups. The resorcinolsulfonic acids (III) or (IV) are, in the second stage of the process, subsequently halogenated to give the halogenoresorcinol sulfonic acids (V) or (VI), respectively. Finally, in the third stage of the process, the halogenoresorcinol sulfonic acids (V) or (VI) are protodesulfonated to give the 2-halogenoresorcinol (I). In this process of protodesulfonation, the groups R and/or $R_1$ which are hydrolyzable at an acidic pH, can be transformed into free functional groups. These various operations and stages of the process of the invention can be carried out in separate stages, separating the intermediate products after each stage, or they can be carried out without interruption and without isolating the intermediates. As noted above, the groups R and/or $R_1$, which may be hydrolyzed in the process of sulfonation or protodesulfonation, are for example acyloxy and acylamine groups.

The procedure of the invention is illustrated in the following reaction scheme.

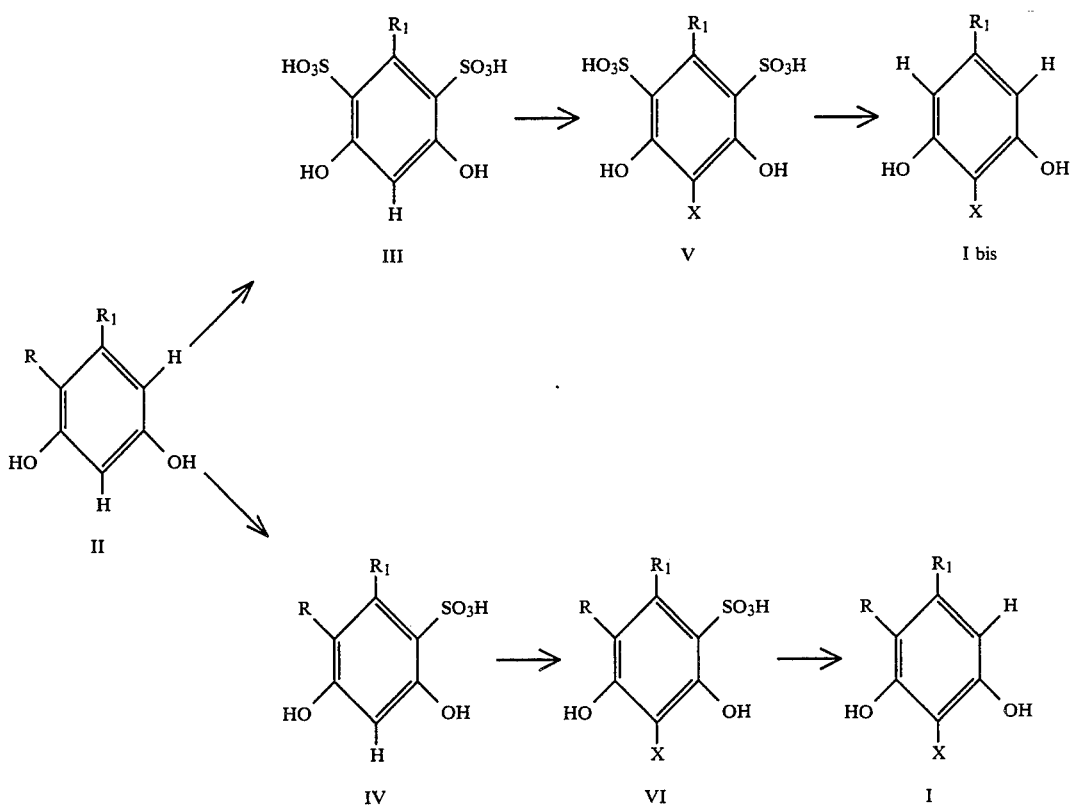

R and/or $R_1$ may also be a halogen atom such as chlorine, bromine, iodine or fluorine.

The esters and ethers of the compounds obtainable by the procedure of the present invention of formula (I) are The procedure for the preparation of 2-halogenoresorcinols according to the present invention, consists, therefore, in (a) sulfonating a resorcinol or derivatives thereof of formula II

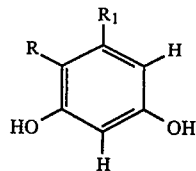

where R and $R_1$ have the same significance as for formula I; (b) halogenating the sulfonation product thus obtained; (c) protodesulfonating the thus obtained halogenation product; and, if desired, functionally modifying free functional groups and/or in liberating functional groups from the corresponding modified functional groups, and/or in interconverting among themselves, free or modified functional groups, and/or in possibly converting an obtained product into one of its salts.

Sulfonation, the first stage of the procedure, may be effected by a per se known sulfonation procedure. For instance, the starting compound resorcinol II can be treated with sulfuric acid with a concentration of between about 90% and 98% or with fuming sulfuric acids with a titer of between about 10% to 20% of free $SO_3$. The reaction should preferably be carried out at a suitable temperature of between about $+5°$ and $+100°$ C. If the starting compound is resorcinol or one of its derivatives with one single substituent $R_1$ other than hydrogen, the resorcinolsulfonic acid III is obtained. On the other hand, if one of the starting products of formula II is used, in which R alone or both the substituents R and $R_1$ are other than hydrogen, the sulfonation product corresponding to formula IV described above is formed, bearing in mind that R and/or $R_1$ may be modified as described above, for instance acyloxy or acylamine R and/or $R_1$ groups may be hydrolyzed to hydroxy or amine groups.

If desired, the resorcinolsulfonic acids of formulas III and IV can be isolated by methods which are themselves per se known. For example, the resorcinolsulfonic acids may be isolated in the form of salts, such as the salts with alkaline or alkaline earth metals, such as sodium, potassium or calcium.

The salts can be obtained in a manner which is per se known, for example by treating the sulfonation mixture with an aqueous solution of a hydroxide, for example, an alkaline hydroxide.

The salts of the resorcinolsulfonic acids may be isolated by a per se known procedure, varying the methods according to the type of acid present and according to the concentration. Many salts, such as the soduim salt of resorcinoldisulfonic acid or of its derivatives, can, for instance, be isolated by filtration or centrifugation. Most of the resorcinolsulfonic acids of formulas III and IV, namely those in which at least one of the substituents R and $R_1$ is other than hydrogen, and their salts, such as alkaline salts, for example sodium salts, are new and also form an object of the present invention.

The halogenation reaction, the second stage of the procedure according to the invention, may be conducted in a manner which is also per se known and may be effected on the sulfonation mixture obtained in the first stage, and possibly also after dilution with water and/or after conversion of the resorcinolsulfonic acids into salts, especially alkaline salts, as described previously. It is also possible, if the halogenation method described below permits, to operate in anhydrous or almost anhydrous conditions, using either free acids or their salts, such as alkaline salts, operating in organic liquids which must be inert towards the reagents used.

For the halogenation reaction, all of the halogenating agents of a phenolic aromatic structure, described in the literature for halogenation reactions with chlorine, bromine, iodine and fluorine, may be used. In this way, should it prove desirable to introduce into the compounds of formula III and/or IV a chlorine or bromine atom, it is possible to use chlorine or bromine as such, operating in acid or basic or neutral conditions. Alternatively, it is possible to cause the formation of chlorine and bromine themselves in the reaction medium (in situ), by either (1) using derivatives which easily yield the halogen and are recommended and described in the literature for chlorination and bromination, such as sulfuryl chloride or sulfuryl bromide, chloro- and bromo-amides or imides; ether perbromides, such as dioxane perbromide; or (2) using an oxidation reduction reaction such as those caused by mixtures of metallic bromides or chlorides (such as alkali metals) and of bromates and chlorates of the same metals in acid aqueous conditions.

For the introduction of iodine, it is preferable to use compounds which liberate the iodine in situ, for instance mixtures of iodides and iodates in aqueous acid conditions.

Fluorination of the compounds of formulas III or IV may be effected, for instance, by treatment with xenon difluoride or perchloryl fluoride ($ClFO_3$) in suitable, preferably anhydrous, conditions.

It has been ascertained that, for chlorination and bromination reactions, operating in aqueous conditions, the halogenation reaction unexpectedly gives good results only when the halogens corresponding to chlorine and bromine are generated in situ, that its, in the same reaction medium and especially in the presence of a suitable quantity of corresponding hydrohalogen acids. On the other hand, when the halogens are used as such, by adding them to the reaction medium, halogenation proceeds with the formation of secondary products which lead to a decrease in the yield and difficulties in the purification of the halogenoresorcinol sulfonic acids and also of the final halogenoresorcinols.

In order, therefore, to obtain with optimal yield the chlorination or bromination of the resorcinolsulfonic acids of formulas III and IV or of their salts, it is necessary to operate in an aqueous solution using chlorine or bromine generated in situ, starting with the above-mentioned reagents, which easily liberate the halogen in the reaction medium or which generate halogen in the reaction medium or which generate halogen by means of an oxidation reduction reaction. In particular, mixtures of diluted hydrochloric acid and an aqueous solution of an alkaline chlorate favor chlorine generation and mixtures of diluted hydrobromic acid and an aqueous solution of an alkaline bromate favor bromine generation. In place of chlorate or bromate, other oxidants such as manganese dioxide can be used.

The chlorination and bromination reactions in aqueous solutions are conducted preferably in the presence of considerable quantities of acids, especially the hydrohalogen acid corresponding to halogen. In particular, operations should be carried out in aqueous solutions containing about 8% to 25% of hydrohalogenacid and the reaction is carried out preferably at a suitable temperature of between about −5° and +10° C. The chlorination and bromination reactions of resorcinolsulfonic acids or their salts, especially the reactions utilizing free halogens, can also be effected in nonaqueous conditions using suitable diluents which do not react with the reagents used in the operative conditions. In this way, for example, it is possible to use nitrobenzene, dimethylformamide, carbon tetrachloride, methylene chloride, concentrated sulfuric acid, etc. or mixtures of the same, such as sulfuric acid and nitrobenzene and sulfuric acid, nitrobenzene and methylene chloride. Small quantities of water (up to about 8%) may also be present in the reaction medium. In order to obtain good yields it is necessary to operate at a temperature of less than 30° C. By using chlorine and bromine as the halogenating agents and diluent mixtures consisting of sulfuricnitrobenzene acid, the temperature at which the best yields are obtained is between about +5° and +25° C.

The mixture obtained from the sulfonation reaction can be directly chlorinated or brominated without isolating the resorcinolsulfonic acids. It is, therefore, sufficient to add a suitable quantity of diluent, such as nitrobenzene, and chlorine or bromine.

The halogenated resorcinolsulfonic acids V and VI are themselves new and novel compounds and also form, together with their salts, a particular object of the present invention. They may be converted into their metallic salts, and in particular into the alkali metal salts, such as potassium or sodium, or alkaline earth metals, such as calcium, by adding the corresponding hydroxides to the acid aqueous solutions obtained by diluting the mixture obtained from the halogenation reaction with water. In addition, if desired, the salts may be isolated, for example, by crystallization, which can be achieved by concentration of the reaction mixture.

Protodesulfonation, the third step of the process of the invention, which causes the transformation of the halogenoresorcinolsulfonic acids V and VI into the 2-halogenoresorcinols I is achieved by the action, on these acids, of aqueous acids, at temperatures which may vary preferably between room temperature and 150° C. Mineral acids are used for this purpose, such as aqueous solutions of sulfuric acid between 20% and 40% or 36% hydrochloric acid, or diluted organic acids, such as halogenated lower aliphatic acids, such as trifluoroacetic or monochloracetic acid or lower aliphatic sulfonic or monocyclic aromatic acids, such as p-toluenesulfonic acid, in aqueous solution, for instance at concentrations of between 20% and 90%, or in a suitable solvent, such as aqueous acetic acid (90%). The duration of hydrolysis depends on the temperature and on the acid used and may vary between 1 and 24 hours. The protodesulfonation reaction may be carried out directly on the mixture obtained from the halogenation reaction, without isolating the halogenoresorcinolsulfonic acids, operating at the above-mentioned acid concentrations.

One particularly advantageous method of effecting protodesulfonation in the procedure of the invention consists of diluting the halogenation mixture with water, in particular of chlorination or bromination, removing any organic solvent which may be present in a per se known manner, and then hydrolyzing the product thus obtained as described previously.

The 2-halogenoresorcinols I resulting from the protodesulfonation of the halogenoresorcinolsulfonic acids are usually found in aqueous solutions and may be separated by per se known procedures. In particular, separation may be effected by extraction with organic solvents, such as chlorinated aliphatic hydrocarbons and especially symmetric dichloroethane and methylene chloride; ethers, especially ethyl ether and methyl tert-butyl ether; alcohols which are only slightly soluble in water, such as amyl alcohols; esters of aliphatic organic acids, such as ethyl acetate and butyl acetate. The 2-halogenoresorcinols I can be subsequently purified, for example by distillation in vacuum and/or converted into their salts, for example into alkaline metal salts, such as potassium or sodium salts which may be isolated in a per se known manner.

The product 2-chlororesorcinol is, like resorcinol, extremely soluble in water (the solubility of 2-chlororesorcinol at 25° C. in water is 350 mg/ml). The inventors surprisingly ascertained, however, that unlike resorcinol, 2-chlororesorcinol is not very soluble in acid aqueous solutions, in particular, at room temperature in sulfuric acid solutions of concentrations of between 20% and 60% (at higher concentrations partial sulfonation takes place) and in concentrated sulfate acid solutions or other inorganic salts such as the neutral salts or possibly acid salts of alkaline metals or alkaline earth metals or of magnesium or ammonium salts of the hydroacids, such as chloride, of phosphoric acids, of nitric acid, or organic acids, such as aliphatic acids with a maximum of 7 carbon atoms, such as acetic or chloroacetic acid. For example, the solubility of 2-chlororesorcinol in aqueous $H_2SO_4$ at 25° C.: $H_2SO_4$ at 20% is 77 mg/ml; $H_2SO_4$ at 30% is 35 mg/ml).

For this reason, 2-chlororesorcinol can be separated very conveniently by extraction or precipitation by first of all treating its aqueous solutions with acids or salts such as those previously mentioned. This separation of 2-chlororesorcinol, independently from the procedures described previously, also forms one of the objects of the present invention.

If the halogenoresorcinols prepared according to the procedure of the present invention contain functional groups, the halogenoresorcinols can be transformed into their derivatives by functional modification by per se known methods, or the functional groups may be liberated in derivatives of this type obtained by the procedure of the invention. In addition, the free or modified functional groups can be transformed one into the other. These reactions can be carried out in a manner which is per se known. In order to modify functional groups present in the above mentioned hydrocarbon groups and/or aromatic functional groups R and/or $R_1$ leaving intact the two hydroxyl groups which appear in formula I, it is necessary to choose suitable methods which allow this type of selective conversion.

To esterify aliphatic or aromatic carboxylic groups, the acids are converted into their salts, for example into alkaline salts, and halogenated hydrocarbons are reacted with them. The corresponding amides are obtained by treatment of the esters with ammonia or amine. The primary or secondary amine functional groups can be alkylated by treatment with alkyl halogens or other alkyl esters such as neutral sulfates or alkyl acids, or by reductive alkylation with appropriate aldehydes, such as formaldehyde and formic acid. It is also possible to prepare quaternary ammonium salts.

On the other hand, it is possible to liberate, by known methods, functional groups of the products I obtained according to the procedure of the invention, should they in fact contain functional modified groups utilizing known methods. For example, the hydroxyl functions can be obtained by acid hydrolysis of the ethereal functional groups or, possibly, also by reductive scission, or by acid or alkaline hydrolysis of the esterified hydroxyl groups. The carboxylic functional groups can be obtained by alkaline or acid hydrolysis of the esters.

The possible conversion of a functional group into another functional group may be effected according to per se known methods. For example, it is possible to transform an aromatic primary amine group into a hydroxyl group or into a halogen by passing through diazonium salts by means of well known reactions of aromatic compound chemistry, or to transform an aliphatic primary amine group into hydroxyl with nitrous acid.

The present invention also includes modifications of the above-mentioned procedure, according to which the procedure is interrupted at any given stage or started with an intermediate compound from which the remaining stages are carried out, or where starting products are formed in situ. The following examples illustrate, in a nonlimiting way, the procedures of the present invention.

EXAMPLE 1

Preparation of the resorcinol-4,6-sulfonic acid (sulfonation)

In one 500 ml ball containing 156 ml of sulfuric acid at 96% (m/m) 52.5 g of resorcinol are added. Before the resorcinol completely dissolves, another 156 ml of sulfuric acid at 96% and another 52.5 g of resorcinol are added. The temperature of the mass tends to increase but does not exceed the maximum temperature of 90°. When the temperature is stable or tends to decrease the mass is heated to 110° and this temperature is maintained for two hours. Then the mass is cooled to room temperature.

By thin layer chromatography analysis it is possible to determine that in the reaction mixture there is no resorcinol while the main constituent is the resorcinol-4,6-disulphonic acid with only small quantities of resorcinol monosulphonic acid and resorcinol trisulphonic acid. The cellulose thin layer chromatography analysis is done with an eluent mixture formed by isoamyl alcohol, pyridine, water, acetic acid (2:2:1:1), (Rf=0.25).

The separation of the resorcinol 4,6-disulphonic acid can be done by precipitation of the acid from the reaction mixture by adding concentrated hydrochloric acid.

EXAMPLE 2

Preparation of the 2-chlororesorcinol-4,6-disulphonic acid. (chlorination with chlorate and hydrochloric acid).

The reaction mixture obtained from Example 1 is poured into a two liter ball containing 472 g of ice and 480 ml of concentrated hydrochloric acid at 37% (m/m). The temperature of the mixture is cooled to −15° C. and, slowly, 60 g of potassium chlorate are added (this operation should proceed very slow and last 12 hours). The reaction mixture is allowed to reach room temperature and, after ten hours from the end of the addition of the chlorate, a solution formed by 127.5 g of KOH and 127 g of water is added. After twelve hours the suspension which is at room temperature is filtered.

The solid remaining on the filter is formed by the potassium salt of the 2-chlororesorcinol-4,6 disulfonic acid - 229 g. Cellulose thin layer chromatography, eluent: isoamyl alcohol, pyridine, water, acetic acid (2:2:1:1). Rf=0.46.

EXAMPLE 3

Preparation of the 2-chlororesorcinol. (Protodesulphonation with diluted $H_2SO_4$).

The potassium salt of the 2-chlororesorcinol-4,6-sulphonic acid (229 g) obtained from Example 2 is treated with 1975 ml of water and 427 g of sulfuric acid at 96% (m/m). The suspension thus obtained is refluxed for 24 hours.

By thin layer chromatography, it is possible to determine in the reaction mixture the presence of small quantities of resorcinol while mainly the 2-chlororesorcinol (86 g) is present. The chromatography analysis is done on a silica layer by an eluting mixture formed by methylene chloride/acetic acid (90:10). Rf=0.77.

EXAMPLE 4

Extraction and purification of 2-chlororesorcinol

The reaction mixture obtained from Example 3 is treated with 350 g of $H_2SO_4$ at 96%, obtaining in this way a sulfuric acid solution having a concentration of about 30% m/m. The solution is brought to room temperature and then extracted wtih butyl acetate.

The butyl acetate solution is evaporated and a residual of 85.5 g of 2-chlororesorcinol is obtained. Crystals from dichloroethane have a melting point of 97° C.

EXAMPLE 5

Preparation of the 2-chlororesorcinol without separation of the intermediates (sulphonation, chlorination with chlorine, protodesulphonation).

The reaction mixture obtained from Example 1 is brought to 15° C. and 120 g of chlorine are then added, always maintaining a temperature of 15° C. The mixture is then poured into a 2 liter ball containing 450 g of ice and 400 ml of water, and to the resulting aqueous phase is firstly added a solution formed by 150 ml of water and 76 g of sodium hydroxide, and then it is refluxed for 24 hours.

The solution is brought to room temperature, and after extraction by ethyl ether, ether evaporation and crystallization of the residual from dichloroethane, 88 g of 2-chlororesorcinol (M.P. 97° C.) are obtained.

EXAMPLE 6

Preparation of the 2-chlororesorcinol without separation of the intermediates (sulphonation, chlorination with chlorine in presence of nitrobenzene, protodesulphonation).

To the reaction mixture obtained from Example 1, 200 ml of nitrobenzene are added and, keeping a constant agitation, the temperature is brought to 60° C. After 15 minutes, the temperature is cooled to 15° C. and 120 g of chlorine are added, always maintaining a temperature of 15° C. The reaction mixture is then poured into a separating funnel containing 450 g of ice and 400 ml of water, the organic phase is separated and the aqueous phase is put in a 2 liter ball.

Firstly, to the aqueous phase is added a solution formed by 150 ml of water and 76 g of sodium hydroxide, and then the resulting mixture is fluxed for 24 hours.

The solution is then brought to room temperature and, after extraction with ethyl ether, evapoation of the ether and crystallization of the residual from dichloroethane, 93 g of 2-chlororesorcinol (M.P. 97° C.) are obtained.

EXAMPLE 7

Preparation of the 2-chlororesorcinol without separation of the intermediates (sulphonation, chlorination with chlorine in presence of nitrobenzene and methylene chloride, protodesulphonation).

To the reaction mixture obtained from Example 1, 200 ml of nitrobenzene are added and, keeping a constant agitation, the temperature is brought to 60° C. After 15 minutes the temperature is cooled to 15°, 50 ml of methylene chloride are then added and, subsequently, 100 g of chlorine are added, always maintaining a temperature of 15° C.

The reaction mixture is then poured into a separating funnel containing 450 g of ice and 400 ml of water, the organic phase is separated and the aqueous phase is put into a 2 liter ball. Firstly, to the aqueous phase is added a solution formed by 150 ml of water and 76 g of sodium hydroxide, and then the resulting mixture is refluxed for 24 hours. The solution is then brought to room temperature and, after extraction with ethyl ether, evaporation of the ether and crystallization of the residual from dichloroethane, 103 g of 2-chlororesorcinol (M.P. 97°) are obtained.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A process for the preparation of a 2-halogenoresorcinol of the formula:

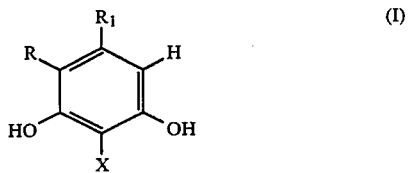

(I)

where X represents a halogen atom and R and $R_1$ may be the same or different and represent a hydrogen atom or a free organic functional or functionally modified group or a hydrocarbon group which may be substituted by one or more free organic functional or functionally modified groups and R and $R_1$ jointly may also represent a free organic functional or functionally modified group or a hydrocarbon group which may be substituted by one or more free organic functional or functionally modified groups, and esters, ethers, and salts thereof, the process comprising:

(a) sulfonating resorcinol or a derivative thereof of the formula:

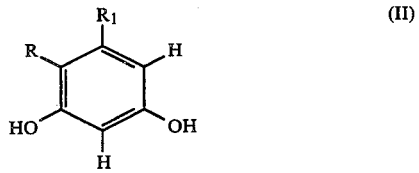

(II)

wherein R and $R_1$ are as defined above for formula (I) to produce a sulfonation product;

(b) halogenating the said sulfonation product to produce a halogenation product, and (c) protodesulfonating the said halogenation product.

2. A process according to claim 1, wherein said sulfonation is effected by treatment with sulfuric acid with a concentration of between about 90% and 98% or with fuming sulfuric acid with a titer of between about 10% and 20% of free $SO_3$.

3. A process according to claim 2, wherein said sulfonation is conducted in a medium which is diluted with an aqueous solution of an alkaline hydroxide.

4. A process according to claim 3, wherein the alkaline salts of said resorcinolsulfonic acids are isolated by precipitation and filtration.

5. A process according to claim 1, wherein the sulfonation mixture produced by said sulfonation step is directly subjected to chlorination, bromination or iodination.

6. A process according to claim 5, wherein said sulfonation mixture is diluted with water prior to halogenation.

7. A process according to claim 1, wherein said sulfonation product is isolated as a resorcinolsulfonic acid or a salt thereof, and halogenated in an anhydrous or essentially anhydrous condition.

8. A process according to claim 5, wherein said chlorination is performed with the addition of free chlorine under acidic, base or neutral conditions, or with compounds which form chlorine under said reaction conditions.

9. A process according to claim 5, wherein said bromination is performed with the addition of free bromine under acidic, basic or neutral conditions, or with compounds which form bromine under said reaction conditions.

10. A process according to claim 5, wherein said chlorination, bromination or iodination is effected under aqueous conditions with chlorine, bromine or iodine generated in situ and in the presence of a suitable quantity of a corresponding hydrohalogen acid.

11. A process according to claim 10, wherein said chlorination is effected in a mixture of hydrochloric acid and an alkali metal chlorate.

12. A process according to claim 11, wherein said bromination is effected in a mixture of hydrobromic acid and an alkali metal bromate.

13. A process according to claim 11, wherein the halogenation is effected at temperatures of between about $-5°$ and $+10°$ C.

14. A process according to claim 7, wherein said halogenation is carried out in the presence of sulfuric acid or a mixture of sulfuric acid and at least one inert solvent.

15. A process according to claim 14, wherein said halogenation is carried out in a mixture of concentrated sulfuric acid and nitrobenzene.

16. A process according to claim 14, wherein said chlorination or bromination is effected with the sulfonation mixture after the addition of nitrobenzene and methylene chloride at a tempperature of below 30° C.

17. A process according to claim 7, wherein the isolated resorcinolsulfonic acid is fluorinated with xenon fluoride and fluoryl perchlorate.

18. A process according to claim 1, wherein protodesulfonation of the halogenation product is effected with aqueous acids at a temperature of between about room temperature and 150° C.

19. A process according to claim 18, wherein said protodesulfonation is effected with sulfuric acid at a concentration of between about 20% and 40% or 36% hydrochloric acid.

20. A process according to claim 10, wherein the halogenation mixture produced by said halogenation step is diluted with water, any organic solvent which may be present is removed, and then said halogenation mixture is directly protodesulfonated.

21. A process according to claim 1, wherein said 2-halogenresorcinol of formula I is further modified by removing one or both of said R and $R_1$, substituting both of said R and $R_1$ with a substituent group $R_2$ wherein $R_2$ has the same definition as for R and $R_1$ defined above, converting one or both of said R and $R_1$ into a different substituent R' and $R_1'$ wherein R' and $R_1'$ have the same definition as for R and $R_1$ defined above, or preparing an ester, ether or salt of said 2-halogenoresorcinol of formula (I).

22. A process according to claim 21, wherein R and $R_1$ represent a member selected from the group consisting of a free hydroxyl group, a modified hydroxy group, a free carboxylic group, a modified carboxylic group, a free amine group, a modified amine group and a halogen.

23. A process according to claim 22, wherein said modified hydroxyl group is an esterified or etherified hydroxyl group.

24. A process according to claim 22, wherein said modified carboxylic group is an esterified carboxylic group.

25. A process according to claim 22, wherein said amine group is a primary, secondary or tertiary group and said modified amine group is an acylated amine group.

26. A process according to claim 1, wherein said hydrocarbon group has between 1 and 12 carbon atoms.

27. A process according to claim 26, wherein said hydrocarbon group is an alkyl group with between 1 and 7 carbon atoms or a cycloalkyl group with between 3 and 7 carbon atoms in the ring and which may be substituted with between 1 and 3 alkyl groups having a maximum of 4 carbon atoms.

28. A process according to claim 21, wherein either or both R and $R_1$ represent a hydroxy group and said hydroxy groups are etherified or esterified.

29. A process according to claim 21, wherein either or both R and $R_1$ represent a carboxylic group and said carboxylic groups are esterified or converted into amide groups.

30. A process according to claim 21, wherein either or both R and $R_1$ represent primary or secondary amine groups which are alkylated to produce a tertiary amine.

31. A process according to claim 30, wherein said tertiary amine is converted into a quaternary ammonium salt.

32. A process according to claim 21, wherein either or both R and $R_1$ represent a hydroxyl group and said hydroxyl groups are etherified with a lower aliphatic alcohol having between 1 and 7 carbon atoms or with a benzyl or phenylethyl alcohol, or said hydroxyl groups are esterified with an organic acid having between 1 and 15 carbon atoms.

33. A process according to claim 22, wherein said amine group is a secondary or tertiary amine group derived from an aliphatic hydrocarbon having between 1 and 7 carbon atoms.

* * * * *